(12) United States Patent
Nagao et al.

(10) Patent No.: US 10,702,675 B2
(45) Date of Patent: Jul. 7, 2020

(54) CATHETER FOR INSERTION INTO BRANCHED BLOOD VESSEL

(71) Applicant: TERUMO CLINICAL SUPPLY CO., LTD., Kakamigahara-shi, Gifu (JP)

(72) Inventors: Shigeyoshi Nagao, Gifu (JP); Tomoyuki Murata, Konan (JP); Koji Ono, Gifu (JP); Iku Hamuro, Fujinomiya (JP)

(73) Assignee: TERUMO CLINICAL SUPPLY CO., LTD., Kakamigahara-Shi, Gifu (JP)

( * ) Notice: Subject to any disclaimer, the term of this patent is extended or adjusted under 35 U.S.C. 154(b) by 161 days.

(21) Appl. No.: 15/819,842

(22) Filed: Nov. 21, 2017

(65) Prior Publication Data

US 2018/0093068 A1 Apr. 5, 2018

Related U.S. Application Data

(63) Continuation of application No. PCT/JP2015/065124, filed on May 26, 2015.

(51) Int. Cl.
*A61M 25/00* (2006.01)
*A61M 25/09* (2006.01)
(Continued)

(52) U.S. Cl.
CPC .......... *A61M 25/005* (2013.01); *A61M 25/00* (2013.01); *A61M 25/0023* (2013.01);
(Continued)

(58) Field of Classification Search
CPC .. A61M 2025/0042; A61M 2025/0046; A61M 2025/0047; A61M 2025/0059;
(Continued)

(56) References Cited

U.S. PATENT DOCUMENTS 6,451,005 B1 9/2002 Saitou et al.
10,299,757 B2 * 5/2019 Yamashita ............... A61B 8/12
(Continued)

FOREIGN PATENT DOCUMENTS

EP 1 712 247 A1 10/2006
EP 2 213 325 A1 8/2010
(Continued)

OTHER PUBLICATIONS

The extended European Search Report dated Dec. 18, 2018, by the European Patent Office in corresponding European Patent Application No. 15893297.0-1132. (10 pages).
(Continued)

*Primary Examiner* — Quynh-Nhu H. Vu
(74) *Attorney, Agent, or Firm* — Buchanan Ingersoll & Rooney PC

(57) ABSTRACT

A branch blood vessel insertion catheter has a catheter body having a lumen penetrating therethrough from a distal end of the catheter body to a proximal end thereof to allow a guide wire to be inserted therethrough. The catheter body has an inner layer, a wire-wound reinforcing member provided on an outer surface of the inner layer, and an outer layer covering both the inner layer and the reinforcing member. The catheter body has a first physical property change point located at a position apart from a distal end of the catheter at a distance of 3.0 to 7.0 mm and a rigidity of a portion of the catheter body located proximally from the first physical property change point is set higher than that of a portion of the catheter body located distally from the first physical property change point.

13 Claims, 6 Drawing Sheets

(51) Int. Cl.
*A61M 25/01* (2006.01)
*A61M 25/06* (2006.01)

(52) U.S. Cl.
CPC .... *A61M 25/0045* (2013.01); *A61M 25/0053* (2013.01); *A61M 25/0054* (2013.01); *A61M 25/0108* (2013.01); *A61M 25/09* (2013.01); *A61M 25/0012* (2013.01); *A61M 25/0041* (2013.01); *A61M 2025/0042* (2013.01); *A61M 2025/0046* (2013.01); *A61M 2025/0047* (2013.01); *A61M 2025/0059* (2013.01); *A61M 2025/0681* (2013.01); *A61M 2205/0216* (2013.01); *A61M 2210/1071* (2013.01)

(58) Field of Classification Search
CPC .. A61M 2025/0681; A61M 2205/0216; A61M 2210/1071; A61M 25/00; A61M 25/0012; A61M 25/0023; A61M 25/0041; A61M 25/0045; A61M 25/005; A61M 25/0053; A61M 25/0054; A61M 25/0108; A61M 25/09
See application file for complete search history.

(56) References Cited

U.S. PATENT DOCUMENTS

| | | | | |
|---|---|---|---|---|
| 2002/0156460 | A1* | 10/2002 | Ye | A61L 29/085 604/534 |
| 2004/0243102 | A1* | 12/2004 | Berg | A61M 25/0013 604/525 |
| 2006/0229589 | A1* | 10/2006 | Itou | A61M 25/0041 604/526 |
| 2007/0149927 | A1 | 6/2007 | Itou et al. | |
| 2009/0030400 | A1* | 1/2009 | Bose | A61M 25/0023 604/510 |
| 2010/0160862 | A1 | 6/2010 | Howat et al. | |
| 2010/0331821 | A1 | 12/2010 | Itou et al. | |
| 2015/0231360 | A1* | 8/2015 | Watanabe | A61M 25/0053 604/527 |
| 2017/0197059 | A1 | 7/2017 | Toyota et al. | |

FOREIGN PATENT DOCUMENTS

| | | |
|---|---|---|
| EP | 3 153 204 A1 | 4/2017 |
| JP | 2001-218851 A | 8/2001 |
| JP | 2004-526529 A | 9/2004 |
| JP | 2006-051081 A | 2/2006 |
| JP | 2006-158788 A | 6/2006 |
| JP | 2007-000358 A | 1/2007 |
| JP | 2008-229160 A | 10/2008 |
| JP | 2013-208150 A | 10/2013 |
| WO | WO 2005/056100 A1 | 6/2005 |
| WO | WO 2007/013545 A1 | 2/2007 |
| WO | 2014/076748 A1 | 5/2014 |

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) dated Nov. 28, 2017, in the corresponding International Application No. PCT/JP2015/065124. (8 pages).
International Search Report (PCT/ISA/210) dated Sep. 1, 2015, by the Japan Patent Office as the International Searching Authority for International Application No. PCT/JP2015/065124.
Written Opinion (PCT/ISA/237) dated Sep. 1, 2015, by the Japan Patent Office as the International Searching Authority for International Application No. PCT/JP2015/065124.

* cited by examiner

CATHETER FOR INSERTION INTO BRANCHED BLOOD VESSEL

TECHNICAL FIELD

The present invention relates to a branch blood vessel insertion catheter to be inserted into a small-diameter blood vessel from a mother blood vessel from which the small-diameter blood vessel branches.

BACKGROUND ART

In recent years, catheter-using medical treatment of a vascular lesion is actively carried out because this medical treatment gives patients very low surgical invasions. There are proposals of catheters which can be inserted into a vascular system having a narrow and complicated pattern with a quick and reliable selectivity. Such catheters are proposed as disclosed in the following patent documents: Japanese Patent Application Laid-Open Publication No. 2001-218851 (patent document 1), Japanese Patent Application Laid-Open Publication No. 2006-51081 (patent document 2), Japanese Patent Application Laid-Open Publication No. 2006-158788 (patent document 3), and Japanese Patent Application Laid-Open Publication No. 2013-208150 (patent document 4).

PRIOR ART DOCUMENTS

Patent Documents

Patent document 1
  Japanese Patent Application Laid-Open Publication No. 2001-218851 (U.S. Pat. No. 6,451,005)
Patent document 2
  Japanese Patent Application Laid-Open Publication No. 2006-51081
Patent document 3
  Japanese Patent Application Laid-Open Publication No. 2006-158788
Patent document 4
  Japanese Patent Application Laid-Open Publication No. 2013-208150

SUMMARY OF THE INVENTION

Problems to be Solved by the Invention

In treating lesions to be carried out by using the catheter, for example, in treating the liver, there is a case in which an operator is demanded to insert the catheter into a small-diameter branch blood vessel branching from a mother blood vessel (hepatic artery) from which the branch blood vessel branches. In this case, as a surgical procedure, the catheter is introduced into the mother blood vessel along a guide wire which has been inserted into the mother blood vessel and the distal end portion of which has reached the branch blood vessel. In the surgical procedure, in an operation of inserting the distal end of the catheter into the branch blood vessel, there is a case in which owing to the rigidity of the distal region of the catheter, the distal end portion of the guide wire inserted into the branch blood vessel is separated from the branch blood vessel.

There is no disclosure of the recognition of the above-described problem in the above-described patent documents 1 through 4. The present inventors have earnestly investigated the structural property of the catheter and developed a catheter capable of solving the above-described problem.

It is an object of the present invention to provide a branch blood vessel insertion catheter which does not cause the distal end portion of a guide wire to separate from a branch blood vessel and thus a distal region of the catheter can be inserted into the branch blood vessel easily and securely in inserting the distal region of the catheter into the branch blood vessel along a guide wire which has been inserted into the mother blood vessel and the distal end portion of which has reached the branch blood vessel.

Means for Solving the Problems

The above-described object can be achieved by the means described below.

A branch blood vessel insertion catheter to be inserted into a branch blood vessel branching from a first blood vessel by passing said catheter through a blood vessel branch from said first blood vessel has a catheter body having a lumen penetrating therethrough from a distal end of said catheter body to a proximal end thereof to allow a guide wire to be inserted therethrough, said catheter body has an inner layer, a wire-wound reinforcing member provided on an outer surface of said inner layer, and an outer layer covering both said inner layer and said reinforcing member; and said catheter body has a first physical property change point located at a position apart from a distal end of said catheter at a distance of 3.0 to 7.0 mm; and a rigidity of a portion of said catheter body located proximally from said first physical property change point is set higher than that of a portion of said catheter body located distally from said first physical property change point.

MODE FOR CARRYING OUT THE INVENTION

Figure 1:
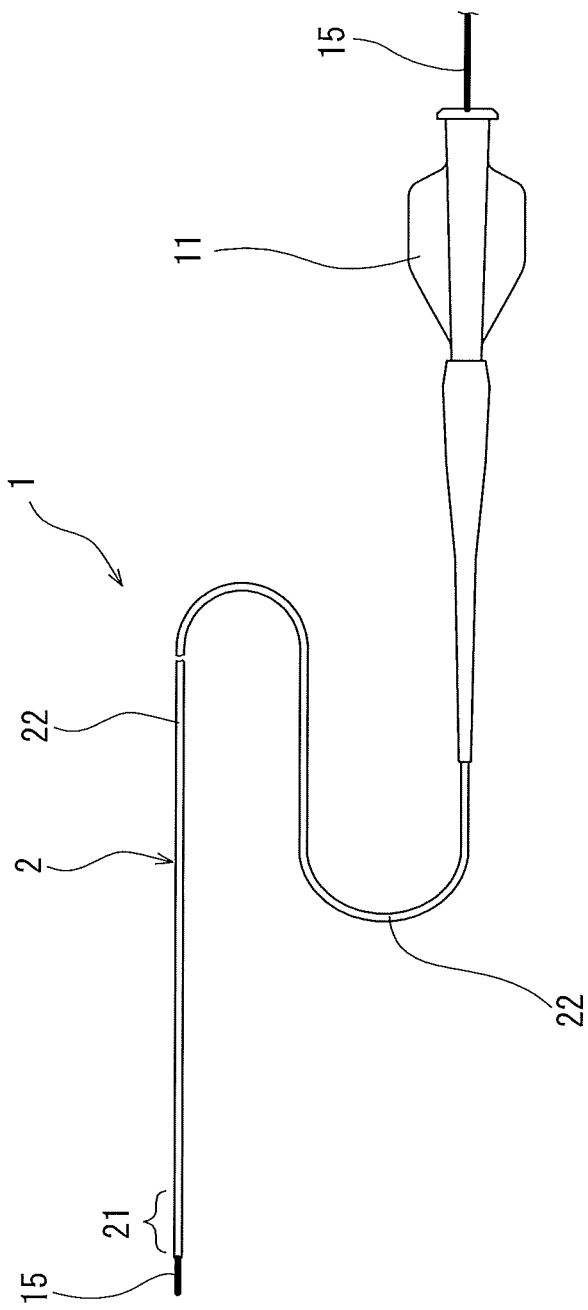
FIG. 1 is a partly abbreviated outside view of a state in which a guide wire is inserted through a branch blood vessel insertion catheter of one embodiment of the present invention.

The branch blood vessel insertion catheter of the present invention is described below by using the embodiments shown in the drawings.

The branch blood vessel insertion catheter of the present invention is inserted into a small-diameter branch blood vessel 52 branching from a first blood vessel 51 by passing the branch blood vessel insertion catheter through a blood vessel branch from the first blood vessel 51.

The branch blood vessel insertion catheter 1 has a catheter body 2 having a lumen 20 penetrating therethrough from a distal end thereof to a proximal end thereof to allow a guide wire 15 to be inserted therethrough. The catheter body 2 has an inner layer 3, a wire-wound reinforcing member 5 provided on an outer surface of the inner layer 3, and an outer layer 4 covering both the inner layer 3 and the reinforcing member 5. The catheter body 2 has a first physical property change point 6 located at a position apart from a distal end of the catheter 1 at a distance of 3.0 to 7.0 mm. The rigidity of a portion of the catheter body located proximally from the first physical property change point 6 is set higher than that of a portion of the catheter body located distally therefrom. An easily bending portion is formed of the portions of the catheter body 2 located distally and proximally from the first physical property change point 6.

The branch blood vessel insertion catheter 1 of the present invention is inserted into a small-diameter branch blood vessel branching from a first blood vessel (for example, hepatic artery) by passing the branch blood vessel insertion catheter through the first blood vessel (hepatic artery) and a branch at which the branch blood vessel branches from the first blood vessel. The branch blood vessel insertion catheter 1 of the present invention is especially effective in a case where it is used as a microcatheter in which the outer diameter of the distal end portion is not more than 1.0 mm. The branch blood vessel insertion catheter of the present invention is more effective in a case where it is used as a microcatheter in which the outer diameter of the distal end portion is not more than 0.7 mm.

The branch blood vessel insertion catheter 1 of this embodiment is composed of the catheter body 2 having the lumen 20 penetrating therethrough from its distal end to proximal end and a hub 11 fixed to the proximal end of the catheter body 2.

The catheter body 2 has the inner layer 3, the wire-wound reinforcing member 5 formed on the outer surface of the inner layer 3, and the outer layer 4 covering the inner layer 3 and the reinforcing member 5.

The catheter body 2 has the first physical property change point 6 located at a position apart from the distal end of the catheter 1 at the distance of 3.0 to 7.0 mm. The rigidity of the portion of the catheter body located proximally from the first physical property change point is set higher than that of the portion of the catheter body located distally therefrom. The easily bending portion is formed of the portions of the catheter body 2 located distally and proximally from the first physical property change point 6. The easily bending portion is more likely to form the center of bending of the catheter body than other portions thereof located distally and proximally from the first physical property change point 6. The easily bending portion means not a bending point, but an easily bendable region formed of the portions of the catheter body located distally and proximally from the first physical property change point 6.

Because the catheter body has the easily bending portion, when a distal end surface of the catheter 1 or a distal end side thereof contacts the inner wall of the branch blood vessel in a state in which the distal end of the guide wire has entered the branch blood vessel with the guide wire being in penetration through the catheter body, the catheter 1 bends at the first physical property change point 6 located at the position apart from the distal end of the catheter at the distance of 3.0 to 7.0 mm. Thereby it does not occur that the distal end of the catheter 1 deforms forward and downward and that the distal end portion of the guide wire which has entered the branch blood vessel is separated therefrom.

Figure 2:
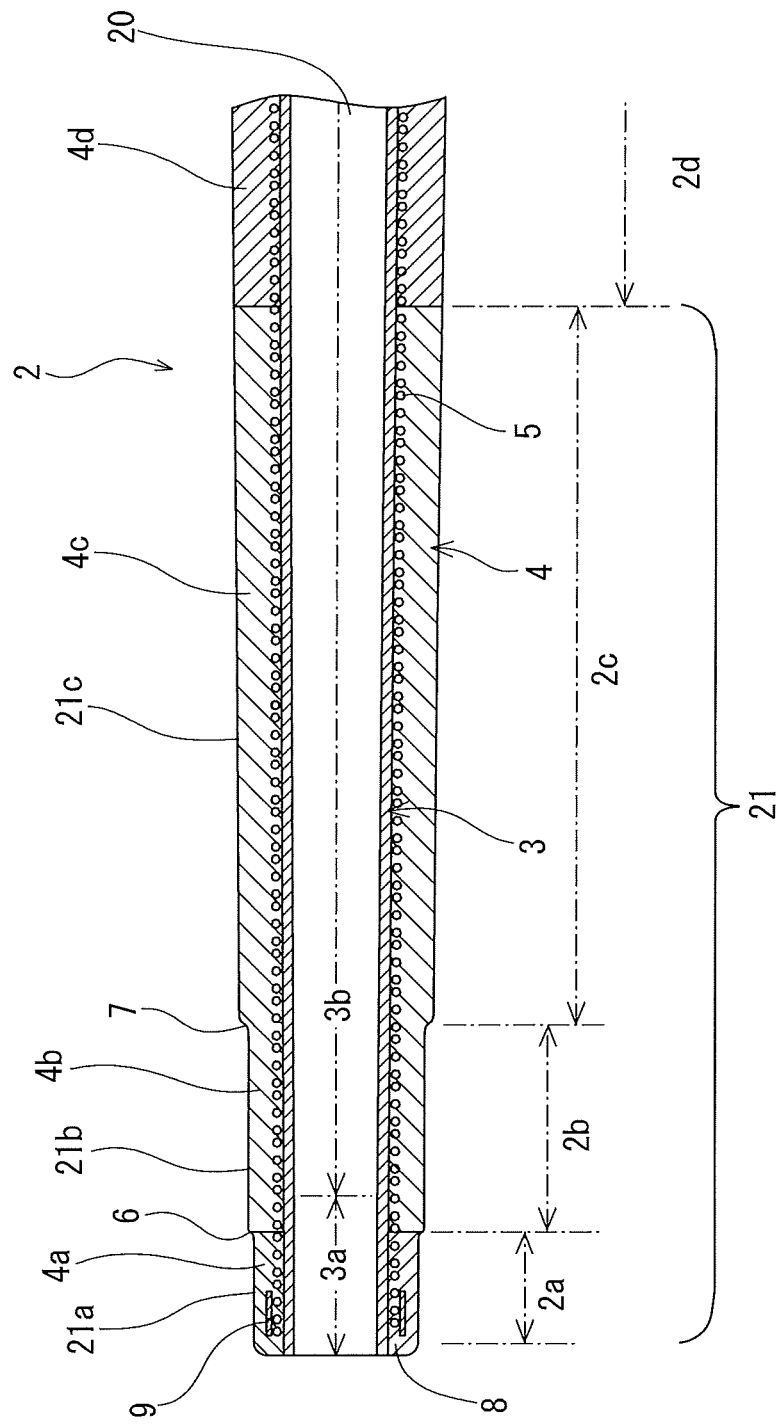
FIG. 2 is an enlarged sectional view of a distal region of the branch blood vessel insertion catheter shown in FIG. 1.

As shown in FIG. 2, in the catheter 1 of this embodiment, the wire-wound reinforcing member 5 has a first winding condition part extended from the distal end of the catheter body 2 toward the proximal end side thereof beyond the first physical property change point 6. The outer layer 4 has a first resin formed part 4a, extended from the distal end of the catheter body 2, which is formed of a first resin and a second resin formed part 4b which is extended from a proximal end of the first resin formed part 4a toward the proximal end side of the catheter body 2 and formed of a second resin more rigid than the first resin. The first physical property change point 6 is formed of a boundary portion between the first resin formed part 4a and the second resin formed part 4b. Thus, the boundary portion is located at the position apart from the distal end of the catheter 1 at a distance of 3.0 to 7.0 mm. It is favorable to locate the boundary portion at a position apart from the distal end of the catheter 1 at a distance of 4.0 to 6.0 mm and more favorable to locate the boundary portion at a position apart from the distal end thereof at a distance of 4.5 to 5.5 mm.

The catheter body 2 is concretely described below. The catheter body 2 has a distal region 21 and a body region 22.

The catheter body 2 has the inner layer 3, the outer layer 4, and the reinforcing member 5 all extended throughout the entire catheter body. In the catheter 1 of this embodiment, the inner layer 3 forms the inner surface form of the inner lumen 20 formed to insert the guide wire therethrough and that of the catheter body 2. The inner layer 3 is formed of the same material and extended in a substantially uniform thickness from the distal end of the catheter body to the proximal end thereof. The inner layer 3 has a distal same inner diameter part 3a extended from the distal end of the catheter body to a portion thereof a little beyond the first physical property change point 6, a distal side inner diameter tapered part 3b extended at a predetermined length from a proximal end of the distal same inner diameter part 3a toward the proximal end side of the catheter body, and a proximal side same inner diameter part which has a substantially equal outer diameter and is extended from a proximal end of the distal side inner diameter tapered part 3b to the proximal end of the catheter body.

The inner diameter of the distal same inner diameter part 3a of the inner layer 3 is set to favorably 0.35 to 0.50 mm and more favorably 0.40 mm to 0.46 mm. The axial length of the distal same inner diameter part 3a of the inner layer 3 is set to preferably 5 to 10 mm. It is preferable to locate the proximal end of the distal same inner diameter part 3a of the inner layer 3 at a position proximal from the proximal end of the first physical property change point 6 at a distance of 1.0 to 4.0 mm.

It preferable to set the inner diameter of the distal end of the distal side inner diameter tapered part 3b of the inner layer 3 substantially equally to the inner diameter of the distal same inner diameter part 3a, the inner diameter of the proximal end of the distal side inner diameter tapered part 3b to 0.53 to 0.65 mm, and increase the inner diameter of the distal side inner diameter tapered part 3b smoothly in a tapered shape in a direction from its distal end to proximal end. It is favorable to set the axial length of the distal side inner diameter tapered part 3b of the inner layer 3 to 60 to 200 mm and more favorable to set the axial length thereof to 70 to 150 mm.

It is favorable to set the thickness of the inner layer 3 to 0.003 to 0.1 mm and more favorable to set the thickness thereof to 0.005 to 0.05 mm.

In this embodiment, the inner layer 3 is formed of the same material entirely from its distal end to proximal end. As materials for forming the inner layer 3, it is preferable to use hard resin including fluororesin such as PTFE and ETFE; polyimide, polyester (for example, polyethylene terephthalate, polybutylene terephthalate), polyolefin (for example, ultra-high molecular weight polyethylene, polypropylene), polyamide, modified polyethylene ether polyamide imide, polyether imide, polystyrene sulfide, and liquid crystal polymer. Fluorine-based polymers such as the PTFE and the ETFE capable of forming an inner surface having a low friction property are preferable.

The wire-wound reinforcing member 5 is formed by winding a wire around an outer surface of the inner layer 3. It is preferable to wind a thin wire consisting of a metal wire around the outer surface of the inner layer reticulately and spirally. It is preferable to compose the wire-wound reinforcing member 5 of meshed braid formed by interweaving thin wires. More specifically, it is preferable to compose the braid of a plurality of small-diameter wires wound at certain intervals in a first spiral direction around the outer surface of the inner layer 3 along the axial direction of the inner layer 3 and a plurality of small-diameter wires wound at certain intervals in a second spiral direction different from the first spiral direction around the outer surface of the inner layer along the axial direction thereof by crossing both groups of the small-diameter wires with each other.

As the wire for forming the wire-wound reinforcing member, metal wires are preferably used. As the metal wires, a stainless steel wire, an amorphous alloy wire, and x-ray contrast metal wires such as a platinum wire, a gold wire, a tungsten wire, a tantalum wire, and an iridium wire are preferable. The amorphous alloy wire formed by using an iron-silicon-boron alloy, a cobalt-silicon-boron alloy or an iron-cobalt-chromium-molybdenum-silicon-boron alloy is preferably used. As the x-ray contrast metal wires, the tungsten wire is preferable. It is preferable to set the diameter of the wire for forming the wire-wound reinforcing member to 0.01 to 0.05 mm.

The wire-wound reinforcing member 5 has the first winding condition part extended from the distal end of the catheter body 2 toward the proximal end side of the catheter body beyond the first physical property change point 6. In the catheter of this embodiment, the first winding condition part is extended toward the proximal end of the catheter body beyond a second physical property change point 7 to be described later. It is to be noted that in the first winding condition part, the same wire is used, that the wire is wound at an equal pitch, and that the same wire-winding form is used. In the catheter body 2, the first winding condition part is extended toward the proximal end side of the catheter body beyond a third resin-formed part 4d extended from a proximal end of a second resin formed part 4c of the catheter toward the proximal end side of the catheter body. The wire-winding pitch in the first winding condition part is set to favorably 0.2 to 0.8 mm and more favorably 0.3 to 0.6 mm.

In the catheter 1 of this embodiment, the outer layer 4 is extended from the distal end of the catheter body to the proximal end thereof, thus forming the outer surface form of the catheter body. The catheter body 2 has a distal side same outer diameter part 2a extended from the distal end thereof to the first physical property change point 6 and a second distal side same outer diameter part 2b extended at a predetermined length in an outer diameter larger than that of the distal side same outer diameter part 2a (in other words, the second distal side same outer diameter part has a large thickness) from a proximal end of the distal side same outer diameter part 2a toward the proximal end side of the catheter body.

In the catheter of this embodiment, the first physical property change point 6 is formed of the boundary portion between the first resin formed part 4a and the second resin formed part 4b. The outer diameter of the catheter body is changed at the boundary portion. The first physical property change point 6 is formed by differentiating the outer diameter of the first resin formed part and that of the second resin formed part from each other and differentiating the hardness of the first resin formed part and that of the second resin formed part from each other. The first physical property change point 6 is located at the position apart from the distal end of the catheter 1 at a distance of 3.0 to 7.0 mm.

The three-point bending load of a portion of a proximal side part 21b (second distal side same outer diameter part 2b) of the catheter disposed in the vicinity of the first physical property change point 6 is set larger than the three-point bending load of a distal side part 21a (distal side same outer diameter part 2a) of the catheter disposed in the vicinity of the first physical property change point 6 by favorably 1.5 to 2.5 times and more favorably 1.7 to 2.3 times. Herein, "three-point bending load" can be measured as described below. A measuring instrument composed of a jig having a horizontal placing surface having a 3 mm gap open upward and a plunger which is formed of a wire having a diameter of 0.85 mm and which has a horizontally extended linear portion at a distal end portion thereof is prepared. The catheter is placed on the horizontal placing surface of the jig in such a way as to pass the catheter above the gap. A portion whose three-point bending load is to be measured is positioned at the gap. The "three-point bending load" can be obtained by measuring a load when the portion whose three-point bending load is to be measured is pushed (when the portion whose three-point bending load is to be measured is curved toward the gap) 0.3 mm at the horizontally extended linear portion of the plunger at a speed of 5 mm/minute.

The three-point bending load of the portion of the distal side part 21a disposed in the vicinity of the first physical property change point 6 is set to favorably 8 to 15 gf and more favorably 9 to 13 gf. The three-point bending load of the portion of the proximal side part 21b disposed in the vicinity of the first physical property change point 6 is set to favorably 16 to 25 gf and more favorably 18 to 23 gf. It is preferable to set the three-point bending load at the first physical property change point 6 to a value in the vicinity of a median between the three-point bending load of the distal side part 21a and that of the proximal side part 21b. More specifically it is preferable to set the three-point bending load at the first physical property change point 6 to 12 to 18 gf.

It is favorable to set the axial length of the first physical property change point 6 to not more than 2.0 mm. The rigidity of the first physical property change point 6 becomes ascendingly higher toward its proximal end side. It is more favorable to set the axial length of the first physical property change point 6 to 0.5 to 2.0 mm and most favorable to set the axial length thereof 0.5 to 1.5 mm.

It is favorable to set the outer diameter of the first distal side same outer diameter part 2a of the catheter body 2 to 0.50 to 0.65 and more favorable to set the outer diameter thereof to 0.52 mm to 0.62 mm. It is favorable to set the axial length of the first distal side same outer diameter part 2a of the catheter body 2 to 3.0 to 7.0 mm, more favorable to set the axial length thereof to 4.0 to 6.0 mm, and most favorable to set the axial length thereof to 4.5 to 5.5 mm. It is preferable to set the thickness of the first distal side same outer diameter part 2a to 0.1 to 0.2 mm.

The outer diameter of the second distal side same outer diameter part 2b of the catheter body 2 is set to favorably 0.55 to 0.70 mm and more favorably 0.57 mm to 0.65 mm. The outer diameter of the second distal side same outer diameter part 2b is set larger than that of the first distal side same outer diameter part 2a favorably by 0.01 to 0.07 mm and more favorably by 0.02 to 0.05 mm. The thickness of the second distal side same outer diameter part 2b is set to favorably 0.05 to 0.15 mm. The thickness of the second distal side same outer diameter part 2b is set larger than that of the first distal side same outer diameter part 2a favorably by not less than 0.005 mm. The axial length of the second distal side same outer diameter part 2b is set to favorably 5.0 to 15.0 mm and more favorably 7.0 to 13.0 mm.

As the second resin, resin having a higher hardness than the first resin is used. It is favorable to set the difference (for example, bending modulus of elasticity ASTM D790) between the hardness of the first resin and that of the second resin to 4 to 15 MPa and more favorable to set the difference therebetween to 5 to 10 MPa.

In the catheter 1 of this embodiment, the catheter body 2 has a second physical property change point 7 located at a position apart from the distal end of the catheter 1 at a distance of 12.0 to 18.0 mm. The rigidity of a portion of the catheter body located proximally from the second physical property change point 7 is set higher than that of a portion of the catheter body located distally therefrom. A second easily bending portion is formed of portions of the catheter body located distally and proximally from the second physical property change point 7. The second physical property change point 7 is located proximally from the first physical property change point 6. The second easily bending portion is a portion more likely to form the center of bending of the catheter body than other portions thereof located distally and proximally from the second physical property change point 7. The second easily bending portion means not a bending point, but an easily bendable region formed of portions of the catheter body located distally and proximally from the second physical property change point 7.

Because the catheter body has the second physical property change point 7, when the portion of the catheter 1 located proximally from the first physical property change point 6 of the catheter 1 and proximately thereto contacts the inner wall of the blood vessel (for example, the vicinity of the portion opposite to the blood vessel-branching portion) in a state in which the distal end of the guide wire has entered the small-diameter branch blood vessel with the guide wire being in penetration through the catheter, the catheter 1 bends at the second physical property change point located proximately to the first physical property change point 6 and proximally therefrom. Thereby the distal end of the catheter 1 can be easily directed toward the blood vessel-branching portion. Further a state in which the distal end of the catheter 1 has entered the branch blood vessel can be securely maintained.

More specifically, in the catheter 1 of this embodiment, the outer layer 4 has the second resin formed part 4b formed of the second resin. The catheter body 2 has a distal side outer diameter tapered part 2c having a starting edge whose outer diameter is larger than that of the second distal side same outer diameter part 2b and is extended proximally at a predetermined length from the starting edge (the proximal end of the second distal side same outer diameter part 2b) toward the proximal end side of the catheter body in a larger diameter than that of the second distal side same outer diameter part 2b.

It is favorable to set the axial length of the second physical property change point 7 to not more than 2.0 mm and the rigidity thereof ascendingly higher from its distal end side toward its proximal end side. It is more favorable to set the axial length of the second physical property change point 7 to 0.5 to 2.0 mm and most favorable to set the axial length thereof 0.5 to 1.5 mm.

In the catheter 1 of this embodiment, as shown in FIG. 2, the distal region 21 of the catheter body 2 has the first distal side same outer diameter part 2a, the second distal side same outer diameter part 2b extended from the rear end of the first distal side same outer diameter part 2a toward the proximal end of the catheter body and having a larger diameter than that of the first distal side same outer diameter part 2a, and the distal side outer diameter tapered part 2c extended from the rear end of the second distal side same outer diameter part 2b toward the proximal end of the catheter body and having a starting edge whose diameter is larger than that of the second distal side same outer diameter part 2b. The first physical property change point 6 is located at the boundary portion between the first distal side same outer diameter part 2a and the second distal side same outer diameter part 2b. The second physical property change point 7 is positioned at the boundary portion between the second distal side same outer diameter part 2b and the distal side outer diameter tapered part 2c.

In the catheter 1 of this embodiment, as shown in FIG. 2, the first winding condition part of the wire-wound reinforcing member 5 is extended toward the proximal end side of the catheter body beyond the second physical property change point 7. The outer layer 4 has the distal side outer diameter tapered part 2c formed in the second resin formed part. The second physical property change point 7 is formed of the starting edge of the diameter-increased part. It is preferable to set the difference between the portion of the catheter body located distally from the second physical property change point 7 and the portion of the catheter body located proximally therefrom to 0.02 to 0.05 mm.

It is favorable to set the three-point bending load of a portion of a proximal side part 21c located in the vicinity of the second physical property change point 7 larger than the three-point bending load of a portion of a distal side part (portion of the proximal side part positioned in the vicinity of the first physical property change point 6) 21b positioned in the vicinity of the second physical property change point by 1.15 to 1.8 times and more favorably by 1.2 to 1.6 times.

It is favorable to set the three-point bending load of the portion of the proximal side part 21c in the vicinity of the second physical property change point 7 to favorably 20 to 45 gf and more favorably 22 to 35 gf. It is favorable to set the three-point bending load of the portion of the distal side part 21b in the vicinity of the second physical property change point 7 to favorably 16 to 25 gf and more favorably 18 to 23 gf. It is favorable to set the three-point bending load at the second physical property change point 7 to a value in the vicinity of a median between the three-point bending load of the distal side part 21b and that of the proximal side part 21c. More specifically, it is favorable to set the three-point bending load at the second physical property change point 7 to 20 to 26 gf.

The second physical property change point 7 (in other words, diameter-increased part) is located at a position apart from the distal end of the catheter 1 at a distance of 12.0 to 18.0 mm. It is preferable to locate the second physical property change point (diameter-increased part) 7 at a position apart from the distal end of the catheter 1 at a distance of 13.0 to 17.0 mm. It is favorable to locate the second physical property change point 7 (diameter-increased part) proximally from the first physical property change point 6 at a distance of 7.0 to 13.0 mm. It is more favorable to locate the second physical property change point 7 (diameter-increased part) proximally from the first physical property change point 6 at a distance of 9.0 to 11.0 mm.

It is preferable to set the outer diameter of the starting edge of the distal side outer diameter tapered part 2c of the catheter body 2 to 0.60 to 0.70 mm and increase the outer diameter of the distal side outer diameter tapered part from its starting edge toward its proximal end smoothly in a tapered configuration. It is favorable to set the outer diameter of the starting edge of the distal side outer diameter tapered part 2c larger than the outer diameter (outer diameter of proximal end) of the second distal side same outer diameter part 2b by 0.02 to 0.07 mm and more favorably by 0.03 to 0.06 mm. The thickness of the starting edge of the distal side outer diameter tapered part 2c is set to favorably 0.07 to 0.17 mm and more favorably 0.08 to 0.14 mm.

It is preferable to set the thickness of the distal side outer diameter tapered part 2c larger than that of the second distal side same outer diameter part 2b by not less than 0.005 mm. The axial length of the distal side outer diameter tapered part 2c is set to favorably 30 to 100 mm and more favorably 40 to 80 mm. It is favorable to set the outer diameter of the terminating edge of the distal side outer diameter tapered part 2c to preferably 0.65 to 0.75 mm. It is favorable to set the outer diameter of the terminating edge of the distal side outer diameter tapered part 2c larger than that of the outer diameter of the starting edge thereof by favorably 0.03 to 0.12 mm and more favorably 0.05 to 0.10 mm.

It is favorable to set the length (the length of the distal region 21) of the catheter 1 of this embodiment from its distal end to the proximal end of the distal side outer diameter tapered part 2c to favorably 70 to 200 mm and more favorably 80 to 150 mm.

In the catheter 1 of this embodiment, the distal region 21 of the catheter body 2 has a uniform inner diameter part 21a, 21b and an inner diameter tapered part 21c extended proximally from a rear end of the uniform inner diameter part 21a, 21b and gradually increasing in its diameter. The first physical property change point 6 is positioned at the uniform inner diameter part 21a, 21b. The second physical property change point 7 is positioned at a distal end portion of the inner diameter tapered part 21c.

At a side proximal from a proximal end of the second resin formed part 4c, the catheter 1 of this embodiment has a third resin formed part 4d which is formed of a third resin having a hardness higher than the second resin and extended proximally at a predetermined length from the proximal end of the second resin formed part 4c. In this embodiment, the third resin formed part 4d forms an intermediate outer diameter tapered part 2d. The intermediate outer diameter tapered part 2d has a starting edge whose outer diameter is equal to that of a terminating edge of the distal side outer diameter tapered part 2c and is thus continuous with the distal side outer diameter tapered part 2c without forming a level difference between the intermediate outer diameter tapered part 2d and the distal side outer diameter tapered part 2c.

Thermoplastic elastomers are preferable as the material to be used to form the outer layer 4. As the thermoplastic elastomers, polyester elastomer (for example, polyethylene terephthalate elastomer), nylon-based elastomer (for example, polyamide elastomer), urethane-based elastomer (for example, polyurethane elastomer), olefin-based elastomer (for example, polyethylene elastomer, polypropylene elastomer), and fluororesin-based elastomer are used. Thermoplastic polyester elastomers are especially preferable.

More specifically, as the thermoplastic polyester elastomers, PELPRENE (registered trademark) P30B, P40B, P40H, P55B, P70B, P90B, P150B, and E450B all produced by Toyobo Co., Ltd. and Hytrel (registered trademark) 3548W, 4047W produced by DU PONT TORAY CO., LTD. are exemplified. As the polyamide elastomer, Pebax 533SA00, 3533SA00, and 4033SA00 produced by Toray Industries, Inc. are exemplified. As the polyurethane elastomer, E380, E385, and E390 produced by Nippon Miractoran Co., Ltd. are exemplified.

It is preferable to use the first, second, and third resins belonging to the same system and having a different hardness.

Figure 4:
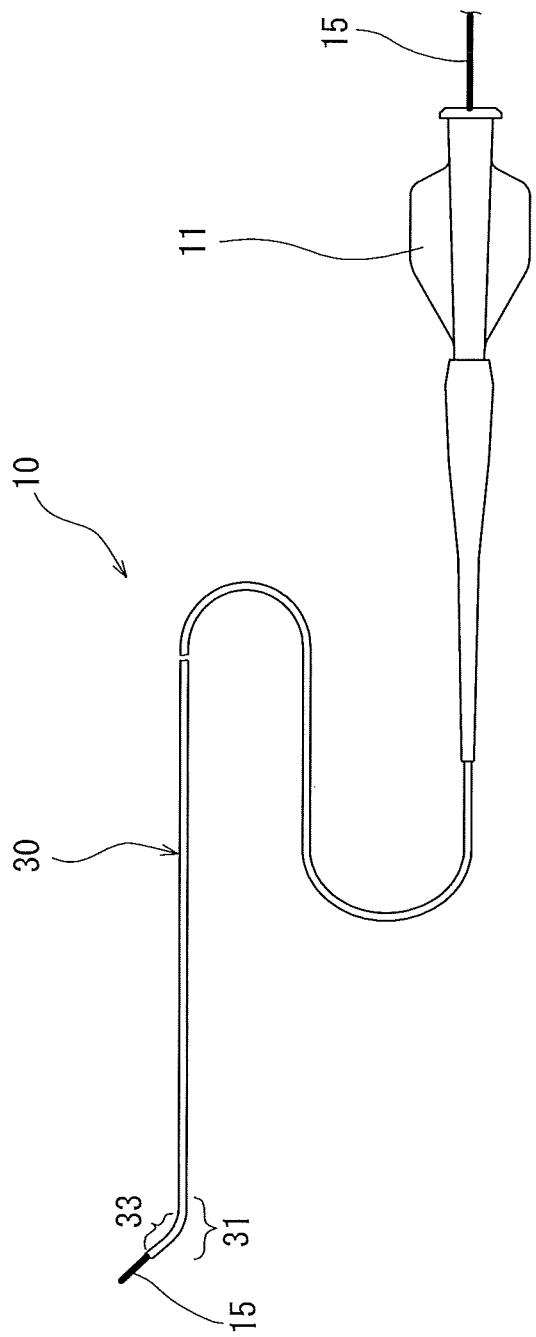
FIG. 4 is a partly abbreviated outside view of a state in which a guide wire is inserted through a branch blood vessel insertion catheter of another embodiment of the present invention.
Figure 5:
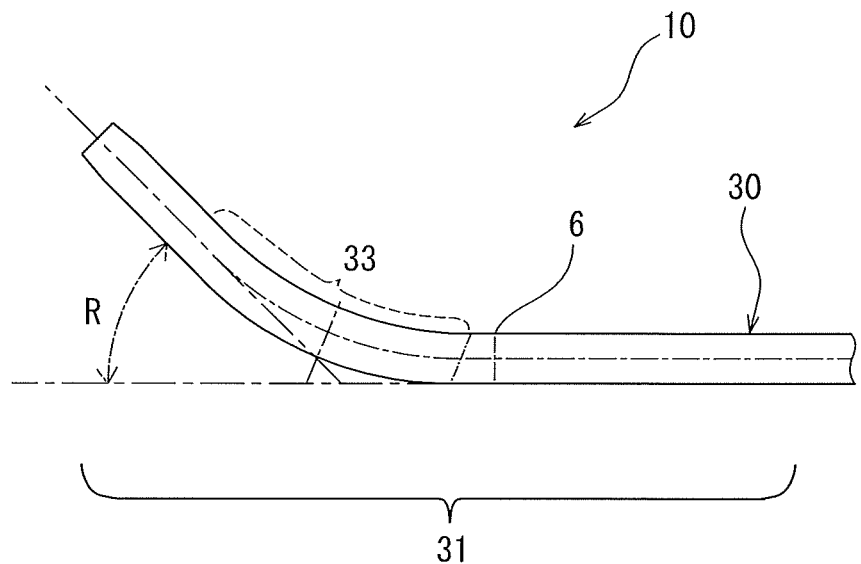
FIG. 5 is an enlarged outside view of a distal region of the branch blood vessel insertion catheter shown in FIG. 4.

Like a catheter 10 of an embodiment shown in FIGS. 4 and 5, the catheter of the present invention may have a curved portion 33 positioned distally from the first physical property change point 6 and having a bending angle of 15 to 75 degrees to the central axis of a catheter body 30. By providing the catheter 10 with the curved portion 33 located distally from the first physical property change point 6, it is easy to insert the distal region of the catheter into a branch blood vessel and move the catheter forward inside the branch blood vessel. It is preferable to set the bending angle of the curved portion 33 to 30 to 60 degrees. It is preferable to dispose the curved portion 33 inside a distal region 31 of the catheter 10 and locate the curved portion 33 at a position intermediate between the distal end of the catheter 10 and the first physical property change point 6 or at a position between the first physical property change point 6 and the position intermediate between the distal end of the catheter 10 and the first physical property change point 6. It is preferable to form the portion of the catheter disposed distally from the curved portion 33 as a straight portion. By disposing the curved portion 33 distally from the first physical property change point 6, the catheter can be easily entered into the blood vessel-branching portion. In addition, a force applied to the distal region 21 of the catheter 10 allows the distal region 21 to bend at the first physical property change point 6 or at the portions distal and proximal from the first physical property change point 6.

In the catheters of all the above-described embodiments, it is preferable to provide the catheter body 2 with a contrast marker 9 so disposed as to encapsulate a distal end of the wire-wound reinforcing member 5. It is preferable to form the contrast marker 9 of an x-ray opaque material (for example, gold, platinum, tungsten or alloys of these metals or silver-palladium alloy, platinum-iridium alloy). By forming the contrast marker in the above-described way, it is possible to confirm the distal end portion of the catheter 1 by x-ray contrast.

In the catheters of all the above-described embodiments, a distal end 8 of the catheter body 2 is formed of the distal end portion of the first resin formed part 4a. The distal end 8 is composed of only the inner layer 3 and the outer layer 4. Neither the reinforcing member 5 nor the marker 9 is present at the distal end 8. In the catheter body 2 of this embodiment, as shown in FIG. 2, neither the reinforcing member 5 nor the marker is formed at the distal end portion of the inner layer 3. The distal end 8 covers the portion of the distal end portion of the inner layer 3 where neither the reinforcing member nor the marker is formed. The axial length of the distal end 8 where neither the reinforcing member nor the marker is formed is set to preferably 0.1 to 0.5 mm.

Figure 3:
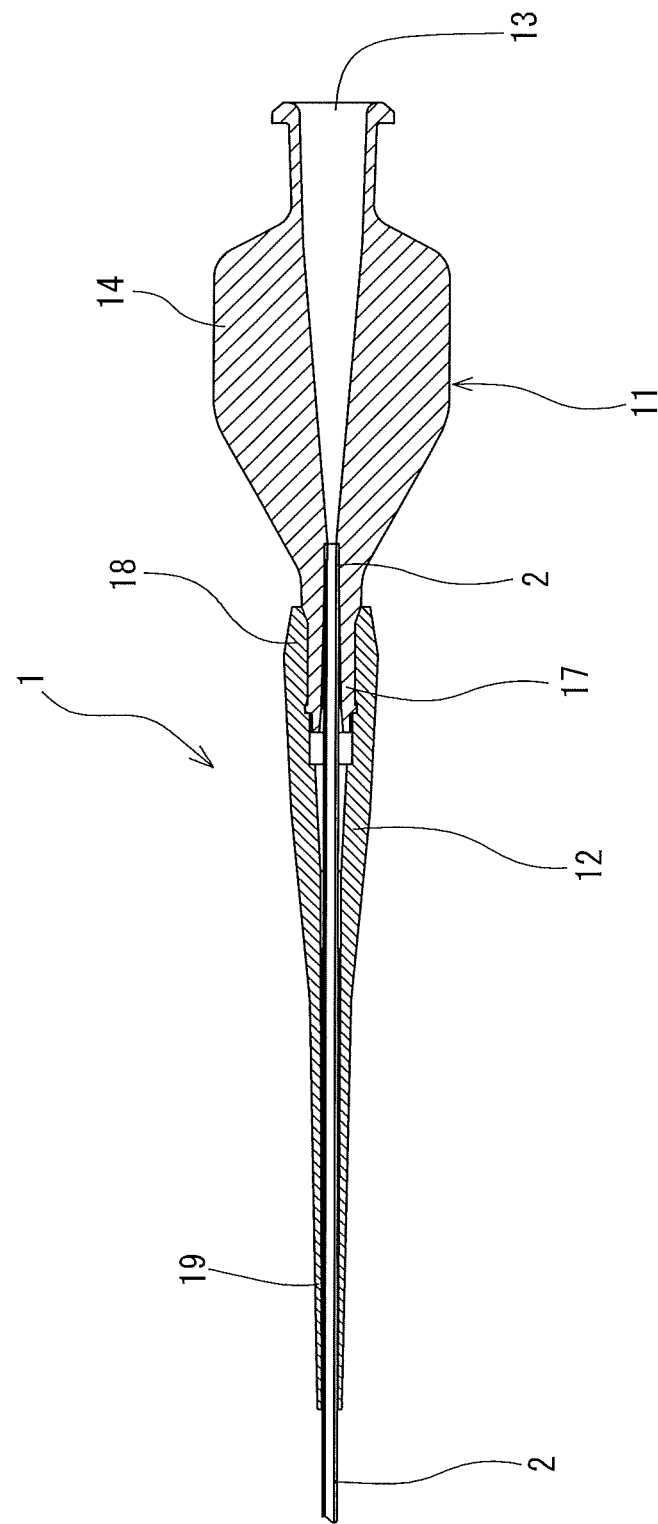
FIG. 3 is an enlarged sectional view of a proximal region of the branch blood vessel insertion catheter shown in FIG. 1

The hub 11 is fixed to the proximal end of the catheter body 2. The hub 11 has a configuration and a construction as shown in FIGS. 1 and 3. More specifically, the hub 11 has an internal passage penetrating therethrough from its distal end to proximal end. The hub has a tubular body part 14 having two wing portions on its sides, a tubular distal end part 17 which is disposed at a distal end of the body part 14 and accommodates the rear end part of the catheter body 2, and a connection part 13 provided at a rear end of the body part 14. A sucking means such as a syringe can be mounted on the connection part 13.

The catheter 1 of this embodiment has a kink prevention tube 12 covering the rear end part of the catheter body 2. The kink prevention tube 12 has a rear part 18 covering the tubular distal end part 17 of the hub 11 and a small-diameter distal end part 19 which projects beyond the body part 14 of the hub 11 and encapsulates the proximal part of the catheter body 2. The distal end part 19 of the kink prevention tube 12 is in close contact with the outer surface of the proximal part of the catheter body 2. By proving the catheter with the kink prevention tube 12, it is possible to prevent the catheter body 2 from kinking at the distal end of the hub 11.

In the catheters 1 of all of the above-described embodiments, it is preferable to subject the outer surface and distal end surface of the outer layer 4 to treatment for allowing them to exhibit lubricity. The treatment includes a method of coating the outer surface and distal end surface thereof with hydrophilic polymer such as polyhydroxy ethyl methacrylate, polyhydroxy ethyl acrylate, hydroxypropyl cellulose, methyl vinyl ether maleic anhydride copolymer, polyethylene glycol, polyacrylamide, polyvinyl pyrrolidone, dimethyl acrylamide-glycidyl methacrylate copolymer or a method of fixing the hydrophilic polymer to the outer surface and distal end surface thereof.

Figure 6:
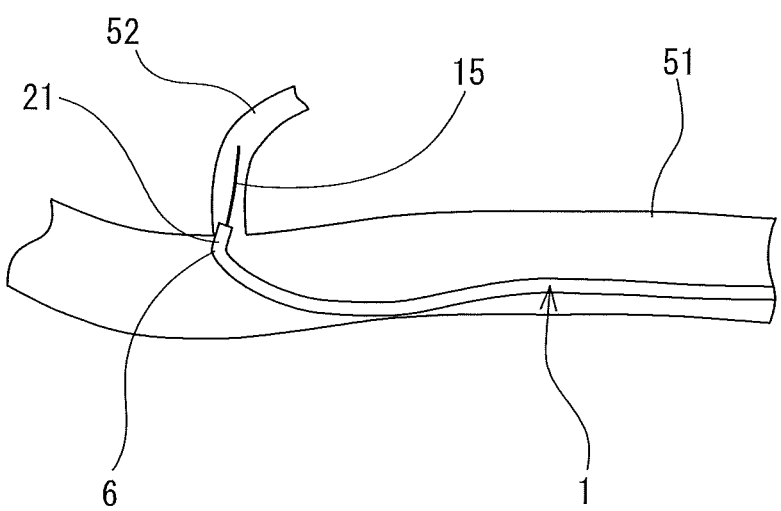
FIG. 6 is an explanatory view for explaining the action of the branch blood vessel insertion catheter of the present invention.
Figure 7:
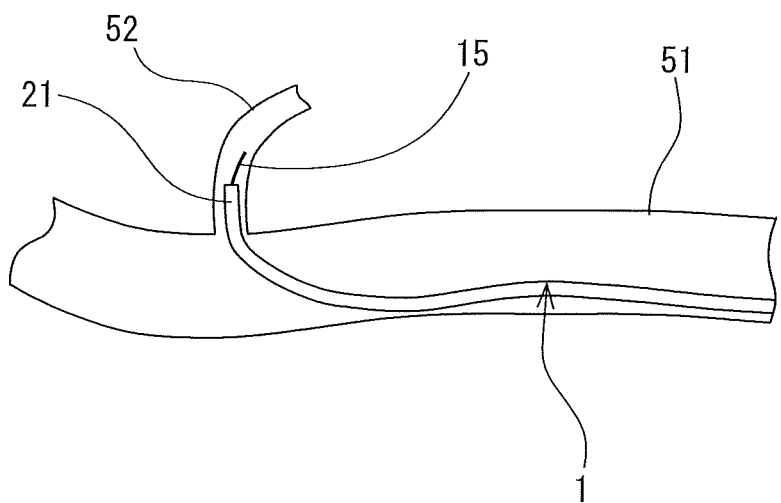
FIG. 7 is an explanatory view for explaining the action of the branch blood vessel insertion catheter of the present invention.
Figure 8:
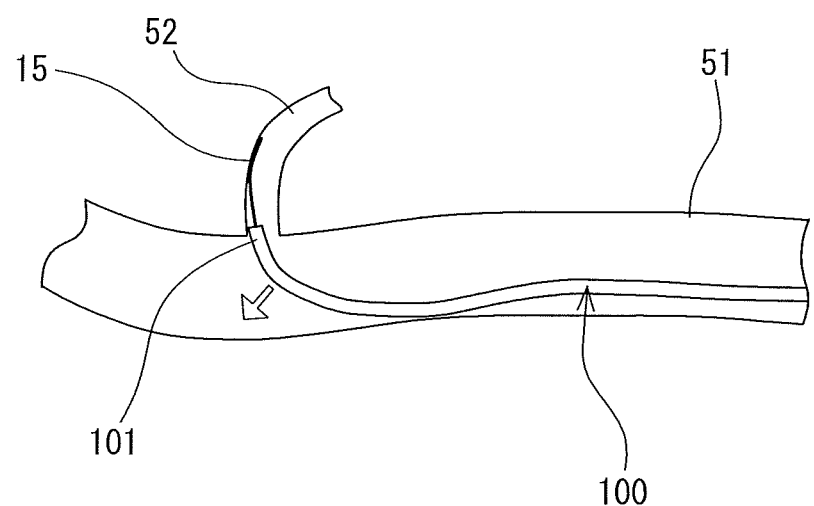
FIG. 8 is an explanatory view for explaining the action of a conventional branch blood vessel insertion catheter.

With reference to FIGS. 6 through 8, the method of operating the branch blood vessel insertion catheter 1 of the present invention is described below by taking a method of inserting it into a branch blood vessel of the hepatic artery as an example.

As shown in FIG. 6, the guide wire 15 is initially inserted into a mother blood vessel 51 of the hepatic artery. Thereafter the distal end portion of the guide wire is inserted into a branch blood vessel 52. After the catheter 1 is inserted into the mother blood vessel 51 of the hepatic artery with the catheter encapsulating the guide wire 15, the distal region of the catheter is inserted into the vicinity of the branch blood vessel 52 in the vicinity of the open portion thereof. In this case, when the distal region of the catheter 1 contacts the inner wall of the branch blood vessel 52, as shown in FIG. 6, the catheter 1 bends easily toward its proximal end at the first physical property change point 6. Because the distal region of the catheter generates a low repulsive force directed toward the distal end thereof in a state in which the catheter has bent, it is possible to prevent the guide wire 15 from being separated from the branch blood vessel 52. By further pressing the catheter 1 forward, the entire distal region 21 of the catheter is inserted into the branch blood vessel 52.

In contrast to the above-described catheter, in a catheter 100 shown in FIG. 8 not having the first physical property change point 6, in a state in which a distal region 101 of the catheter 100 has been inserted into a portion of the branch blood vessel 52 in the vicinity of the opening thereof and curved, the distal region of the catheter 100 generates a repulsive force directed toward the distal end thereof. Thereby as shown in FIG. 8, the distal region of the catheter 100 is pressed against the inner wall of the branch blood vessel and thus there is a high possibility that the distal region of the catheter separates from the branch blood vessel. When the catheter separates from the branch blood vessel, there is a high possibility that the guide wire 15 is separated from the branch blood vessel.

EXAMPLES

Concrete examples of the present invention are described below.

Example 1

A mandrel (core material) consisting of a silver-plated soft copper wire having a distal end part having a diameter of 0.43 mm and a length of 20 mm, a tapered part extended 100 mm from the proximal end of the distal end part toward the proximal side of the mandrel and having a diameter of 0.58 mm at its proximal end, and a body part extended 1600 mm from the proximal end of the tapered part toward the proximal end of the mandrel and having a diameter of 0.58 mm was prepared.

Polytetrafluoroethylene was applied to the core material and molded to form an inner layer having a thickness of 0.01 mm on an outer circumferential surface of the mandrel. Thereafter the outer surface of the inner layer was subjected to chemical treatment with a solution consisting of a glycolic solvent and a solute of naphthalene complex of a sodium salt. Thereafter the distal end part and proximal end part of the core material coated with the inner layer were cut so as to adjust the total length thereof to 1650 mm.

A metal wire of tungsten having a diameter of 0.018 mm was wound around the outer circumference of the inner layer in a length of 300 mm at a pitch of 0.4 m from a position located proximally from the distal end of the inner layer at a distance of 3 mm. Thereafter the metal wire was wound around the outer circumference of the inner layer by stepwise changing the pitch of from 0.4 mm to 1.6 mm to form a wire-wound reinforcing member.

The reinforcing member was formed on the inner layer and outer circumference of the mandrel in this manner. In addition, a thin annular (axial length: 0.5 mm) contrast marker made of a tungsten-iridium alloy was fixed to the distal end of the reinforcing member.

Thereafter an outer layer was formed on the outer circumference of the base material of the catheter.

A first tubular tube having an outer diameter of 0.57 mm and a length of 5 mm was produced in advance. As the material for forming the first tube, a thermoplastic polyester elastomer [bending modulus of elasticity (ASTM D790): 15 MPa, PELPRENE (registered trademark) P30B produced by Toyobo Co., Ltd.] was used.

Similarly, a second tube having a front side part having an outer diameter of 0.61 mm and a length of 10 mm and a tapered part whose outer diameter increased from 0.64 mm to 0.71 mm and whose length was 35 mm was produced. As the material for forming the second tube, the thermoplastic polyester elastomer [bending modulus of elasticity (ASTM D790): 23 MPa, PELPRENE (registered trademark) P40B produced by Toyobo Co., Ltd.] was used.

Similarly, a third tube having a tapered part whose outer diameter increased from 0.65 mm to 0.74 mm and whose length was 60 mm and a proximal side part which had an outer diameter of 0.80 mm and was extended 140 mm toward the proximal end side of the base material of the catheter was produced. As the material for forming the third tube, the thermoplastic polyester elastomer [bending modulus of elasticity (ASTM D790) 108 MPa, PELPRENE (registered trademark) P40B produced by Toyobo Co., Ltd.] was used.

A tapered fourth tube whose outer diameter increased from 0.85 mm to 0.94 mm and which had a length reaching the proximal end of the base material of the catheter was produced. As the material for forming the tapered tube, the thermoplastic polyester elastomer [PELPRENE (registered trademark) P40B produced by Toyobo Co., Ltd.] having a bending modulus of elasticity (ASTM D790) higher than the third resin was used.

The base material of the catheter on which the inner layer, the reinforcing member, and the marker were formed was covered with the first, second, third, and fourth tubes in a direction from its distal end side by arranging the four tubes in the order from the first, second, third, and fourth tube. After the outer surface of the base material of the catheter was covered with a heat-shrinkable tube (FEP) consisting of fluorine-based resin, both end portions thereof were fixed with a stopper. Thereafter the base material was passed through a heat tunnel whose temperature was 340 degrees to melt-adhere adjacent regions of the first through fourth tubes to each other. After the rear end part of the base material where an outer layer was not formed was cut off, the core metal was pulled out from the base material. In this manner, a catheter body was produced.

As pre treatment, a tetrahydrofuran (THF) solution of diphenylmethyl-diisocyanate adjusted to 5.3% was applied to the outer surface of the catheter body. Thereafter the solution was dried at a room temperature for 30 minutes. Thereafter a THF solution of a methyl vinyl ether-maleic acid ethyl ester copolymer (hydrophilic polymer substance) adjusted to 1.65% was applied to the outer surface of the catheter body. Thereafter the THF solution was subjected to drying treatment at a room temperature for 30 minutes to dry the THF solution. A hub was connected to the proximal end of the catheter body to which the hydrophilic polymer substance was imparted. In this manner, the catheter of the present invention was produced.

Comparison Example 1

A cylindrical first tube having an outer diameter of 0.57 mm and a length of 10 mm was produced. Except that the cylindrical first tube was used, the catheter of the comparison example 1 was produced in a manner similar to that of the example 1.

Experiment 1

The three-point bending load at the distal region of the catheter bodies of the example 1 and the comparison example 1 were measured. A jig having a horizontal placing surface having a 3 mm gap open upward and a plunger which is formed of a wire having a diameter of 0.85 mm and which has a horizontally extended linear portion at a distal end portion thereof were used. The catheter is placed on the horizontal placing surface of the jig in such a way as to pass the catheter above the gap. A portion whose three-point bending load was to be measured was positioned at the gap. A load was measured for each catheter body when the portion whose three-point bending load was to be measured was pushed (when the portion whose three-point bending load was to be measured was curved toward the gap) 0.3 mm at the horizontally extended linear portion of the plunger at a speed of 5 mm/minute. A value obtained in this manner was set as the three-point bending load of each catheter body. The load was measured for each catheter body by using a tension universal testing machine (produced by ORIENTEC Inc.: RTC-1210A). The results were as shown in table 1.

TABLE 1

| | Example 1 | Comparison example 1 |
|---|---|---|
| 2.5 mm apart from distal end | 11.1 gf | 11.1 gf |
| 5.0 mm apart from distal end | 14.2 gf | 11.1 gf |
| 10.0 mm apart from distal end | 20.3 gf | 14.2 gf |
| 15.0 mm apart from distal end | 23.1 gf | 20.3 gf |
| 20.0 mm apart from distal end | 27.1 gf | 23.1 gf |
| 25.0 mm from distal end | 27.1 gf | 27.1 gf |

Experiment 2

A silicon tube having an inner diameter of 4 mm, an outer diameter of 8 mm, and a length of 300 mm was prepared as a main tube. A silicon tube having an inner diameter of 1 mm, an outer diameter of 2 mm, and a length of 30 mm was connected to a side hole formed on a side surface of the main tube at 90 degrees with respect to the central axis of the main tube. In this manner, a first blood vessel model having a branch tube was produced.

Similarly, a silicon tube having an inner diameter of 4 mm, an outer diameter of 8 mm, and a length of 300 mm was connected to the proximal end side of the main tube at 75 degrees (branch portion was set to acute angle) with respect to the central axis of the main tube. In this manner, a second blood vessel model having a branch tube was produced.

Similarly, a silicon tube having an inner diameter of 4 mm, an outer diameter of 8 mm, and a length of 300 mm was connected to the proximal end side of the main tube at 60 degrees (branch portion was set to acute angle) with respect to the central axis of the main tube. In this manner, a third blood vessel model having a branch tube was produced.

Similarly, a silicon tube having an inner diameter of 4 mm, an outer diameter of 8 mm, and a length of 300 mm was connected to the proximal end side of the main tube at 45 degrees (branch portion was set to acute angle) with respect to the central axis of the main tube. In this manner, a fourth blood vessel model having a branch tube was produced.

Similarly, a silicon tube having an inner diameter of 4 mm, an outer diameter of 8 mm, and a length of 300 mm was connected to the proximal end side of the main tube at 30 degrees (branch portion was set to acute angle) with respect to the central axis of the main tube. In this manner, a fifth blood vessel model having a branch tube was produced.

A guide wire was inserted into the main tube of each of the first through fifth blood vessel models from the proximal end side of the main tube. The guide wire was advanced inside the main tube until the distal end portion thereof having a length of 3 mm reached the branch tube. Each of the catheters of the example 1 and the comparison example was inserted into each main tube from the proximal end side thereof in such a way that each catheter encapsulates the guide wire to check whether the distal region thereof could be inserted into the branch tubes. The results were as shown in table 2. The symbol o indicates that the distal region of the catheter could be inserted into the branch tube. The symbol x indicates that the distal region of the catheter could not be inserted into the branch tube.

TABLE 2

| Blood vessel model | Example 1 | Comparison example 1 |
| --- | --- | --- |
| First model (branch angle: 90 degrees) | o | o |
| Second model (branch angle: 75 degrees) | o | o |
| Third model (branch angle: 60 degrees) | o | o |
| Fourth model (branch angle: 45 degrees) | o | o |
| Fifth model (branch angle: 30 degrees) | o | x |

INDUSTRIAL APPLICABILITY

The branch blood vessel insertion catheter of the present invention is constructed as follows:

(1) A branch blood vessel insertion catheter to be inserted into a branch blood vessel branching from a first blood vessel by passing said catheter through a blood vessel branch from said first blood vessel; wherein said catheter has a catheter body having a lumen penetrating therethrough from a distal end of said catheter body to a proximal end thereof to allow a guide wire to be inserted therethrough; said catheter body has an inner layer, a wire-wound reinforcing member provided on an outer surface of said inner layer, and an outer layer covering both said inner layer and said reinforcing member; and said catheter body has a first physical property change point located at a position apart from a distal end of said catheter at a distance of 3.0 to 7.0 mm; and a rigidity of a portion of said catheter body located proximally from said first physical property change point is set higher than that of a portion of said catheter body located distally from said first physical property change point.

The branch blood vessel insertion catheter of the present invention is inserted into a small-diameter branch blood vessel branching from a first blood vessel by passing the branch blood vessel insertion catheter through a blood vessel branch from the first blood vessel. The catheter has a catheter body has a lumen penetrating therethrough from a distal end thereof to a proximal end thereof to allow a guide wire to be inserted therethrough. The catheter body has an inner layer, a wire-wound reinforcing member provided on an outer surface of the inner layer, and an outer layer covering both the inner layer and the reinforcing member. The catheter body has a first physical property change point 6 located at a position apart from a distal end of the catheter at a distance of 3.0 to 7.0 mm. The rigidity of a portion of the catheter body located proximally from the first physical property change point is set higher than that of a portion of the catheter body located distally therefrom. Therefore, the easily bending portion is formed of the portions of the catheter body located distally and proximally from the first physical property change point.

The catheter of the present invention has the first physical property change point located at the position apart from the distal end of the catheter at a distance of 3.0 to 7.0 mm. The rigidity of the portion of the catheter body located proximally from the first physical property change point is set higher than that of the portion of the catheter body located distally therefrom. The easily bending portion is formed of the portions of the catheter body located distally and proximally from the first physical property change point. Thus, in inserting the distal region of the catheter into the branch blood vessel along the guide wire which has been inserted into the mother blood vessel and the distal end portion of which has reached the branch blood vessel, the catheter does not cause the distal end portion of the guide wire to separate from the branch blood vessel and thus the distal region of the catheter can be inserted into the branch blood vessel easily and securely.

The above-described embodiments may be carried out as follows:

(2) A branch blood vessel insertion catheter according to the above (1), wherein a three-point bending load of a portion of a proximal side part disposed in a vicinity of said first physical property change point is set larger than that of a portion of a distal side part disposed in said vicinity of said first physical property change point by 1.5 to 2.5 times.

(3) A branch blood vessel insertion catheter according to the above (1) or (2), wherein said first physical property change point has an axial length of not more than 2.0 mm; and a rigidity of said first physical property change point becomes ascendingly higher from a distal end side thereof toward a proximal end side thereof.

(4) A branch blood vessel insertion catheter according to any one of the above (1) through (3), wherein said wire-wound reinforcing member is extended from said distal end of said catheter body toward a proximal end side thereof beyond said first physical property change point; said outer layer has a first resin formed part extended from said distal end of said catheter body or from a position in a vicinity of said distal end of said catheter body and formed of said first resin and a second resin formed part extended from a proximal end of said first resin formed part toward said proximal end side of said catheter body and formed of a second resin more rigid than said first resin; and said first physical property change point is formed of a boundary portion between said first resin formed part and said second resin formed part.

(5) A branch blood vessel insertion catheter according to the above (1) through (3), wherein said catheter body has a curved portion positioned at a side distally from said first physical property change point and having a bending angle of 15 to 75 degrees with respect to a central axis of said catheter.

(6) A branch blood vessel insertion catheter according to any one of the above (1) through (5), wherein said catheter body has a second physical property change point located at a position apart from said distal end of said catheter at a distance of 6.0 to 21.0 mm; and a rigidity of a portion of said catheter body located proximally from said second physical property change point is set higher than that of a portion of said catheter body located distally from said second physical property change point.

(7) A branch blood vessel insertion catheter according to the above (6), wherein said outer layer has a diameter-increased part formed in said second resin formed part; and said second physical property change point is formed of said diameter-increased part.

(8) A branch blood vessel insertion catheter according to the above (6) or (7), wherein a three-point bending load of a portion of a proximal side part located in a vicinity of said second physical property change point is set larger than that of a portion of a distal side part located in said vicinity of said second physical property change point by 1.15 to 1.8 times.

(9) A branch blood vessel insertion catheter according to any one of the above (6) through (8), wherein said second physical property change point has an axial length of not more than 2.0 mm; and a rigidity of said second physical property change point becomes ascendingly higher from a distal end side thereof toward a proximal end side thereof.

(10) A branch blood vessel insertion catheter according to any one of the above (6) through (9), wherein a distal region of said catheter body has a uniform inner diameter part and an inner diameter tapered part extended proximally from a rear end of said uniform inner diameter part and gradually increasing in a diameter thereof; said first physical property change point is positioned in said uniform inner diameter part; and said second physical property change point is positioned at a distal end portion of said inner diameter tapered part.

(11) A branch blood vessel insertion catheter according to any one of the above (6) through (10), wherein said distal region of said catheter body has a first uniform outer diameter part, a second uniform outer diameter part extended from a rear end of said first uniform outer diameter part toward said proximal end of said catheter body and having a larger diameter than that of said first uniform outer diameter part, and a large outer diameter part extended from a rear end of said second uniform outer diameter part toward said proximal end of said catheter body and having a starting edge whose diameter is larger than that of said second uniform outer diameter part; said first physical property change point is positioned at a boundary portion between said first uniform outer diameter part and said second uniform outer diameter part; and said second physical property change point is positioned at a boundary portion between said second uniform outer diameter part and said large outer diameter part.

(12) A branch blood vessel insertion catheter according to any one of the above (6) through (11), wherein said second physical property change point is positioned proximally from said first physical property change point at a distance of 7.0 to 15.0 mm therefrom.

(13) A branch blood vessel insertion catheter according to any one of the above (1) through (12), wherein said catheter body has a contrast marker so disposed as to encapsulate a distal end of said wire-wound reinforcing member.

(14) A branch blood vessel insertion catheter according to any one of the above (1) through (13), which is used together with a guide wire to be introduced into a target branch blood vessel.

(15) A branch blood vessel insertion catheter according to any one of the above (1) through (14), which is a microcatheter in which an outer diameter of a distal end portion is not more than 1.0 mm.

The invention claimed is:

1. A branch blood vessel insertion catheter comprising a catheter body having a lumen penetrating therethrough from a distal end of said catheter body to a proximal end thereof to allow a guide wire to be inserted therethrough;
wherein said catheter body has an inner layer, a wire-wound reinforcing member provided on an outer surface of said inner layer, and an outer layer covering both said inner layer and said reinforcing member,
said catheter body has an outer diameter of a distal end portion is not more than 0.7 mm,
said catheter body has a first physical property change point located at a position apart from a distal end of said catheter at a distance of 3.0 to 7.0 mm and having an axial length not more than 2.0 mm and a rigidity of a portion of said catheter body located proximally from said first physical property change point is set higher than that of a portion of said catheter body located distally from said first physical property change point;
said catheter body has a second physical property change point and a rigidity of a portion of said catheter body located proximally from said second physical property change point is set higher than that of a portion of said catheter body located distally therefrom,
said second physical property change point is formed of a diameter-increased part located at a position apart from said distal end of said catheter at a distance of 12.0 to 18.0 mm or a position apart from said first physical property change point at a distance of 7.0 to 13.0 mm,
said catheter body has an outer diameter difference of 0.02 to 0.05 mm between a portion of said catheter body located distally from said second physical property change point and a portion of said catheter body located proximally therefrom, and an axial length of said second physical property change point is not more than 2.0 mm, and
said catheter is for insertion into a branch blood vessel branching from a first blood vessel and has a first easily bending portion formed of a portion of said catheter body located distally and proximally from said first physical property change point and a second easily bending portion formed of a portion of said catheter body located distally and proximally from said second physical property change point.

2. A branch blood vessel insertion catheter according to claim 1, wherein a three-point bending load of a portion of a proximal side part disposed in a vicinity of said first physical property change point is 18 to 23gf, a three-point bending load of a portion of a distal side part disposed in said vicinity of said first physical property change point is 9 to 13gf, and the three-point bending load of the portion of the proximal side part disposed in the vicinity of said first physical property change point is 1.5 to 2.5 times larger than that of the portion of the distal side part disposed in said vicinity of said first physical property change point.

3. A branch blood vessel insertion catheter according to claim 1, wherein said wire-wound reinforcing member is extended from said distal end of said catheter body toward a proximal end side thereof beyond said first physical property change point; said outer layer has a first resin formed part extended from said distal end of said catheter body or from a position in a vicinity of said distal end of said catheter body and formed of said first resin and a second resin formed part extended from a proximal end of said first resin formed part toward said proximal end side of said catheter body and formed of a second resin more rigid than said first resin; and said first physical property change point is formed of a boundary portion between said first resin formed part and said second resin formed part.

4. A branch blood vessel insertion cathertr according to claim 1, wherein said cathertr body has a curved portion positioned at a side distally from said first physical property change point and having a bending ngle of 15 to 75 degerees with respect to a central axis of said catheter.

5. A branch blood vessel insertion catheter according to claim 1, wherein a three-point bending load of a portion of a proximal side part located in a vicinity of said second physical property change point is 22 to 35gf, a three-point bending load of a portion of a distal side part located in said vicinity of said second physical property change point is 18 to 23gf and the three-point bending load of the portion of the proximal side part located in the vicinity of said second physical property change point is 1.15 to 1.8 times larger than that of the portion of the distal side part located in said vicinity of said second physical property change point.

6. A branch blood vessel insertion catheter according to claim 1, wherein a rigidity of said second physical property change point becomes ascendingly higher from a distal end side thereof toward a proximal end side thereof.

7. A branch blood vessel insertion catheter according to claim 1, wherein a distal region of said catheter body has a uniform inner diameter part and an inner diameter tapered part extended proximally from a rear end of said uniform inner diameter part and gradually increasing in a diameter thereof; said first physical property change point is positioned in said uniform inner diameter part; and said second physical property change point is positioned at a distal end portion of said inner diameter tapered part.

8. A branch blood vessel insertion catheter according to claim 1, wherein a distal region of said catheter body has a first uniform outer diameter part, a second uniform outer diameter part extended from a rear end of said first uniform outer diameter part toward said proximal end of said catheter body and having a larger diameter than that of said first uniform outer diameter part, and a large outer diameter part extended from a rear end of said second uniform outer diameter part toward said proximal end of said catheter body and having a starting edge whose diameter is larger than that of said second uniform outer diameter part; said first physical property change point is positioned at a boundary portion between said first uniform outer diameter part and said second uniform outer diameter part; and said second physical property change point is positioned at a boundary portion between said second uniform outer diameter part and said large outer diameter part.

9. A branch blood vessel insertion catheter according to claim 1, wherein said catheter body has a contrast marker so disposed as to encapsulate a distal end of said wire-wound reinforcing member.

10. A branch blood vessel insertion catheter according to claim 1, which is used together with a guide wire to be introduced into a target branch blood vessel.

11. A branch blood vessel insertion catheter according to claim 1, which is a microcatheter in which an outer diameter of a distal end portion is not more than 1.0 mm.

12. A branch blood vessel insertion catheter according to claim 1, wherein said outer layer has a first resin formed part extended from said distal end of said catheter body or from a position in a vicinity of said distal end of said catheter body and formed of said first resin and a second resin formed part extended from a proximal end of said first resin formed part toward said proximal end side of said catheter body and formed of a second resin more rigid than said first resin, said first physical property change point is formed of a boundary portion between said first resin formed part and said second resin formed part, and said outer layer has said diameter-increased part formed by changing a thickness of said second resin forming portion.

13. A branch blood vessel insertion catheter comprising
a catheter body having a lumen penetrating therethrough from a distal end of said catheter body to a proximal end thereof to allow a guide wire to be inserted therethrough;
wherein said catheter body has an inner layer, a wire-wound reinforcing member provided on an outer surface of said inner layer, and said catheter body has an outer layer covering both said inner layer and said reinforcing member,
said catheter body has an outer diameter of a distal end portion is not more than 0.7 mm,
said catheter body has a first physical property change point located at a position apart from a distal end of said catheter at a distance of 3.0 to 7.0 mm and having an axial length not more than 2.0 mm and a rigidity of a portion of said catheter body located proximally from said first physical property change point is set higher than that of a portion of said catheter body located distally from said first physical property change point;
said catheter body has a second physical property change point and a rigidity of a portion of said catheter body located proximally from said second physical property change point is set higher than that of a portion of said catheter body located distally therefrom,
said outer layer has a diameter-increased part formed with said second resin formed part by changing a thickness of said second resin forming portion,
said second physical property change point is formed said diameter-increased part located at a position apart from said distal end of said catheter at a distance of 12.0 to 18.0 mm or a position apart from said first physical property change point at a distance of 7.0 to 13.0 mm and has an axial length not more than 2.0 mm, and
said catheter is for insertion into a branch blood vessel branching from a first blood vessel and has a first easily bending portion formed of a portion of said catheter body located distally and proximally from said first physical property change point and a second easily bending portion formed of a portion of said catheter body located distally and proximally from said second physical property change point,
a distal region of said catheter body has a uniform inner diameter part and an inner diameter tapered part extended proximally from a rear end of said uniform inner diameter part and gradually increasing in a diameter thereof; said first physical property change point is positioned in said uniform inner diameter part; and said second physical property change point is positioned at a distal end portion of said inner diameter tapered part, and
said distal region of said catheter body has a first uniform outer diameter part, a second uniform outer diameter part extended from a rear end of said first uniform outer diameter part toward said proximal end of said catheter body and having a larger diameter than that of said first uniform outer diameter part, and a large outer diameter part extended from a rear end of said second uniform outer diameter part toward said proximal end of said catheter body and having a starting edge whose diameter is larger than that of said second uniform outer diameter part; said first physical property change point is positioned at a boundary portion between said first uniform outer diameter part and said second uniform outer diameter part; and said second physical property change point is formed of said diameter-increased part positioned at a boundary portion between said second uniform outer diameter part and said large outer diameter part.

* * * * *